(12) United States Patent
Ghajar et al.

(10) Patent No.: US 9,721,476 B2
(45) Date of Patent: Aug. 1, 2017

(54) SYSTEM AND METHOD FOR DYNAMIC COGNITIVE TRAINING

(71) Applicant: Sync-Think, Inc., Boston, MA (US)

(72) Inventors: Jamshid Ghajar, Palo Alto, CA (US); Umesh Rajashekar, New York, NY (US)

(73) Assignee: SYNC-THINK, INC., Boston, MA (US)

( * ) Notice: Subject to any disclaimer, the term of this patent is extended or adjusted under 35 U.S.C. 154(b) by 206 days.

(21) Appl. No.: 14/535,223

(22) Filed: Nov. 6, 2014

(65) Prior Publication Data

US 2015/0126899 A1    May 7, 2015

Related U.S. Application Data

(60) Provisional application No. 61/900,917, filed on Nov. 6, 2013.

(51) Int. Cl.
| | |
|---|---|
| G09B 5/02 | (2006.01) |
| A61B 5/16 | (2006.01) |
| G09B 9/00 | (2006.01) |
| G09B 19/00 | (2006.01) |
| A61B 5/00 | (2006.01) |

(52) U.S. Cl.
CPC .............. *G09B 5/02* (2013.01); *A61B 5/162* (2013.01); *A61B 5/4064* (2013.01); *A61B 5/4088* (2013.01); *A61B 5/4842* (2013.01); *A61B 5/6804* (2013.01); *G09B 19/00* (2013.01)

(58) Field of Classification Search
CPC .............. G09B 19/00; G09B 5/06; A61B 5/16
See application file for complete search history.

(56) References Cited

U.S. PATENT DOCUMENTS

| | | | | |
|---|---|---|---|---|
| 5,883,692 A | * | 3/1999 | Agonis | A61B 3/024 351/224 |
| 6,435,878 B1 | * | 8/2002 | Reynolds | G09B 5/065 434/219 |
| 2006/0270945 A1 | * | 11/2006 | Ghajar | A61B 3/113 600/558 |
| 2007/0027406 A1 | * | 2/2007 | LaPlaca | A61B 5/16 600/558 |

(Continued)

FOREIGN PATENT DOCUMENTS

WO    WO 2014146192 A1    9/2014

*Primary Examiner* — Jeffrey G Hoekstra
*Assistant Examiner* — Patrick Fernandes
(74) *Attorney, Agent, or Firm* — Morgan, Lewis & Bockius LLP

(57) ABSTRACT

A method of visual cognitive training is performed at a device with a display. The method includes sequentially displaying a plurality of visual stimuli in a first region of a subject's field of view. While sequentially displaying the plurality of visual stimuli, the device moves the first region periodically along a predefined path within the subject's field of view. The device prompts the subject to respond to a task associated with the sequential display of the plurality of visual stimuli. The device receives a response to the task associated with the sequential display of the plurality of visual stimuli and records information corresponding to the subject's response to the task associated with the sequential display of the plurality of visual stimuli.

20 Claims, 15 Drawing Sheets

(56) References Cited

U.S. PATENT DOCUMENTS

2009/0130640 A1* 5/2009 Hardy .................... G09B 19/00
 434/236
2014/0359454 A1* 12/2014 Lee ....................... G06F 3/0488
 715/734

* cited by examiner

SYSTEM AND METHOD FOR DYNAMIC COGNITIVE TRAINING

RELATED APPLICATIONS

This application claims priority to U.S. Provisional Patent Application No. 61/900,917, filed Nov. 6, 2013, which is hereby incorporated by reference in its entirety.

TECHNICAL FIELD

The disclosed embodiments relate generally to systems and methods of cognitive training. More specifically, the disclosed embodiments relate to methods and systems for dynamic cognitive training in which subjects use smooth visual pursuit and/or predictive timing.

BACKGROUND

Techniques to enhance "brain fitness" through cognitive training have been employed in a variety of context. However, some evidence suggests that the effects of conventional cognitive training methods fail to transfer to other untrained tasks.

SUMMARY

Accordingly, there is a need for cognitive training methods that provide transferable effects (e.g., transferable to untrained tasks). In accordance with some embodiments, a method, system, and computer-readable storage medium are proposed for dynamic cognitive training in which subjects use smooth visual pursuit and/or predictive timing. For example, in some embodiments, a cognitive training game includes stimuli contained within a region of a display that undergoes predictable movement.

BRIEF DESCRIPTION OF THE DRAWINGS

Like reference numerals refer to corresponding parts throughout the drawings.

DETAILED DESCRIPTION OF EMBODIMENTS

Figure 1:
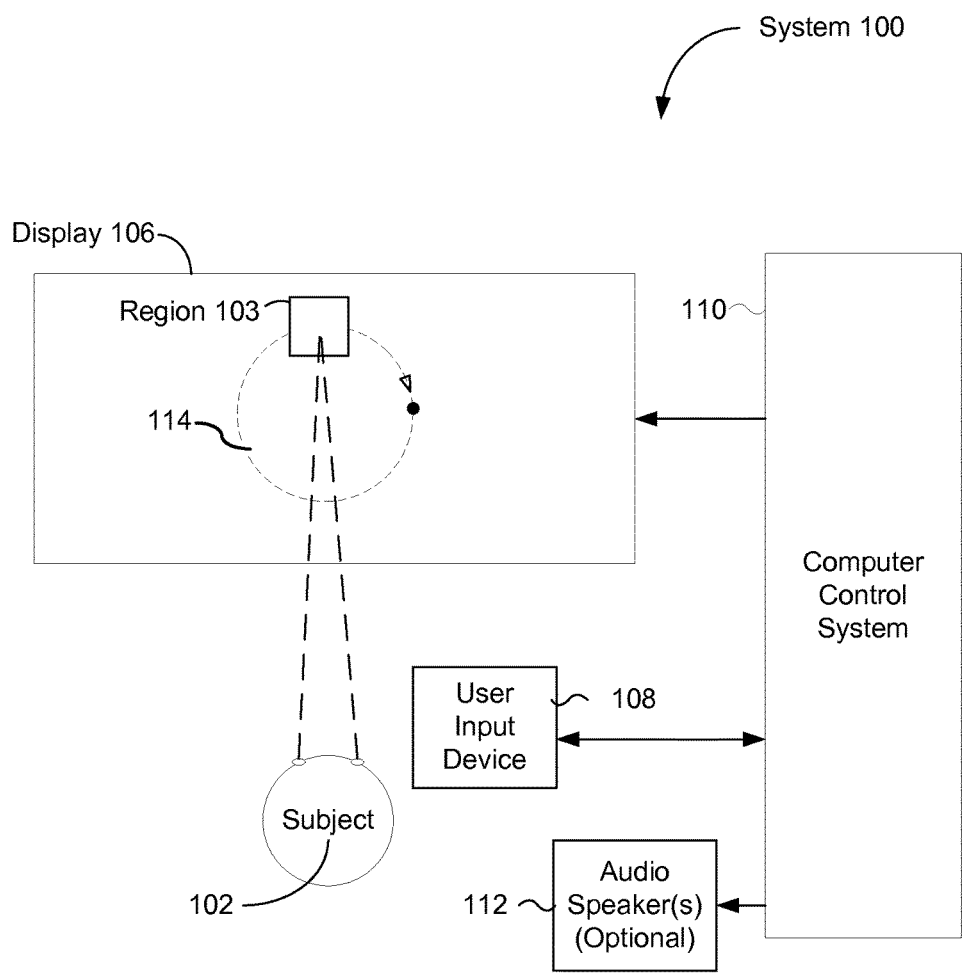
FIG. 1 illustrates a system for dynamic cognitive training, in accordance with some embodiments.

It is very difficult to measure thinking performance without movement by the subject. However, since a similar neural network is used for anticipatory timing, cognition and motor timing are linked. Therefore, diagnosis and therapy can be performed for anticipatory timing difficulties in the motor and cognitive domains using motor reaction times and accuracy. In particular, a subject's performance on a cognitive test (e.g., a cognitive game) that requires the subject to smoothly track visual stimuli can be measured. As discussed below, these measurements can be used for both diagnosis and therapy.

Anticipatory cognition and movement timing are controlled by essentially the same brain circuits. Variability or a deficit in anticipatory timing produces imprecise movements and disrupted thinking, such as difficulty in concentration, memory recall, and carrying out both basic and complex cognitive tasks. Such variability and/or deficit leads to longer periods of time to successfully complete tasks and also leads to more inaccuracy in the performance of such tasks. Accordingly, in some embodiments, performance on such tasks is measured to determine whether a person suffers impaired anticipatory timing. In some embodiments, a sequence of stimuli is presented in a predictable manner to train a person to improve anticipatory timing.

The stimuli can use any sensory modality. In some embodiments, the stimuli are visual stimuli. In other embodiments, the stimuli are auditory. While other forms of stimuli can be used, the embodiments described here use visual stimuli. The subject's responses may be manual or even spoken. In some embodiments, the subject's responses are measured by a mechanical, piezoelectric or other sensors activated by physical movement of the subject, such as pressing a button. In yet other embodiments, a frontal brain electroencephalographic (EEG) signal (e.g., the "contingent negative variation" signal) is measured during the period before a subject's response. The amplitude of the EEG signal is proportional to the degree of anticipation and will be disrupted when there are anticipatory timing deficits.

Described in more detail below are methods and games that, in some circumstances, are used to improve attention and white matter connectivity in brain regions that are associated with attention and working memory. The methods and games are also used to reverse damage to the white matter tracts that subserve predictive timing in patients with traumatic brain injury (TBI) by training TBI patients to execute predictive smooth pursuit eye movements. Although monitoring smooth pursuit eye movements is normally done using eye tracking apparatus, which are expensive and difficult to use, use of a personal computing device obviates the need for an eye tracking apparatus through design of tasks that require the subject to visually track the stimulus effectively in order to perform well in the task. To this end, cognitive games are provided in which stimuli are displayed in a region that moves on a display, for example, along a tracking path at a constant speed. The subject's performance in the cognitive game will be poor if they fail to track the target. As a result, the subject's performance can be monitored and the difficulty of the game adjusted to ensure that subjects are moving their eyes in a predictable pattern.

To this end, in accordance with some implementations, a method of visual cognitive training is performed at a device. The method includes sequentially displaying a plurality of visual stimuli in a first region of a subject's field of view. While sequentially displaying the plurality of visual stimuli, the device moves the first region periodically along a predefined path within the subject's field of view. The device prompts the subject to respond to a task associated with the sequential display of the plurality of visual stimuli. The device receives one or more responses to the task associated with the sequential display of the plurality of visual stimuli and records information corresponding to the subject's one or more responses to the task.

In some embodiments, the first region moves at a speed that is less than a foveating threshold.

In some embodiments, the system includes a personal computing device with a display. The visual stimuli are displayed on the display. Receiving the one or more responses to the task includes receiving one or more user inputs on the personal computing device.

In some embodiments, the displaying, moving, and prompting comprise a cognitive training game. In some embodiments, the cognitive training game is an n-back game, and prompting the subject to respond to the task includes prompting the subject to identify when a respective visual stimulus corresponds to a previous visual stimulus that occurred a predetermined number of visual stimuli prior to the respective visual stimulus. The predetermined number is a load factor. In some embodiments, the system repeats the cognitive training game while varying one or more difficulty parameters associated with the game. The difficulty parameters include one or more of: the load factor, a duration of time for which a respective stimulus in the plurality of stimuli is displayed, and a speed of the movement of the first region.

In some embodiments, recording the information corresponding to the subject's one or more responses includes recording one or more of: a number of correct responses, a number of incorrect responses, a number of correct rejections, and a number of incorrect rejections.

In some embodiments, two or more of the plurality of stimuli include a displayed first circle and a displayed second circle that is concentric with the first circle. In each subsequent stimulus of the two or more stimuli, a size of the first circle is changed relative to a size of the second circle such as to reduce a difference in the size of the first circle and the size of the second circle. Prompting the subject to respond to the task includes prompting the subject to predict a time when the size of the first circle and the size of the second circle would be equal. In some embodiments, prior to the time when the size of the first circle and the size of the second circle would be equal, the system presents at least one stimulus in which display of the first circle has been discontinued.

In some embodiments, the system uses the recorded information to calculate a current performance index for the subject, and compares the current performance index to a baseline performance index for the subject as a diagnostic to measure the effects any of: a traumatic brain injury, intoxication, dementia, and/or fatigue.

In another aspect of the present invention, to address the aforementioned limitations of conventional cognitive training techniques, some implementations provide a non-transitory computer readable storage medium storing one or more programs. The one or more programs comprise instructions, which when executed by an electronic device with one or more processors and memory, cause the electronic device to perform any of the methods provided herein.

In yet another aspect of the present invention, to address the aforementioned limitations of cognitive training techniques, some implementations provide an electronic device. The electronic device includes one or more processors, memory, and one or more programs. The one or more programs are stored in memory and configured to be executed by the one or more processors. The one or more programs include an operating system and instructions that when executed by the one or more processors cause the electronic device to perform any of the methods provided herein.

Reference will now be made in detail to various implementations, examples of which are illustrated in the accompanying drawings. In the following detailed description, numerous specific details are set forth in order to provide a thorough understanding of the present disclosure and the described implementations herein. However, implementations described herein may be practiced without these specific details. In other instances, well-known methods, procedures, components, and mechanical apparatus have not been described in detail so as not to unnecessarily obscure aspects of the implementations.

FIG. 1 illustrates a system 100 for dynamic cognitive training, in accordance with some embodiments. In this example, a plurality of visual stimuli is sequentially displayed in a region 103 on a display 106, which is within a subject's field of view. (The plurality of visual stimuli is not illustrated in FIG. 1, but is rather described in greater detail below.) Display 106 is, optionally, a computer monitor, projector screen, or another display device. For example, in various embodiments, display 106 is a display of a tablet computer, smart-phone, laptop computer, personal computer, smart-television, or the like.

While the plurality of visual stimuli is sequentially displayed, region 103 is moved periodically along a tracking path 114 within the subject's field of view. For example, movement of region 103 is periodic in the sense that region 103 traverses tracking path 114 more than once (e.g., 1.1 times, 2 times, 8 times, etc). At some point (e.g., in real-time, or when giving instructions to the subject prior to the display of the stimuli), the subject is prompted to respond to a task associated with the sequential display of the plurality of visual stimuli. For example, the subject's response(s) may include actuation of a user input device 108, which can be a mouse, button on a keyboard, microphone, joystick, etc. Computer control system 110 records information corresponding to the subject's response(s) and stores corresponding information in memory (e.g., memory 812, FIG. 8, as described below).

The user input device 108 is coupled to a computer control system 110 that controls the display of the stimuli and the movement of region 103. In some implementations, computer control system 110 is optionally coupled with, and controls, one or more audio speaker(s) 112. Display 106 is also coupled to computer control system 110.

In some embodiments, display 106, user input device 108, computer control system 110, and the one or more audio speaker(s) 112 are incorporated into a single housing of an electronic device (for example, a tablet computer). In some embodiments, display 106 is a touch-screen display and user input device 108 is incorporated into display 106. In some implementations, one or more of these components are also used for other device tasks, such as playing music (e.g., audio speaker(s) 112 together with computer control system 110), running mobile applications (e.g., display 106 together with computer control system 110), etc.

Figure 2A:
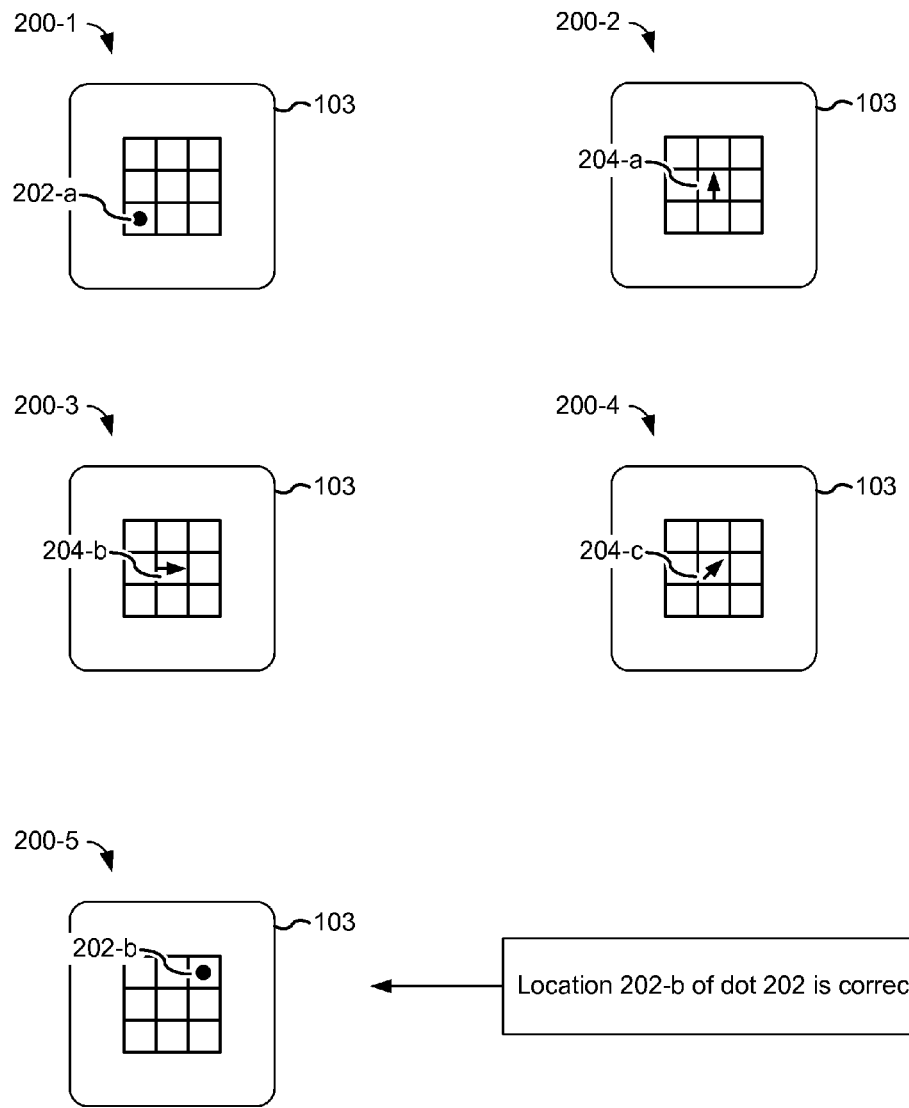
FIGS. 2A-2B illustrate examples of a so-called "spatial working memory" cognitive training game, in accordance with some embodiments.
Figure 2B:
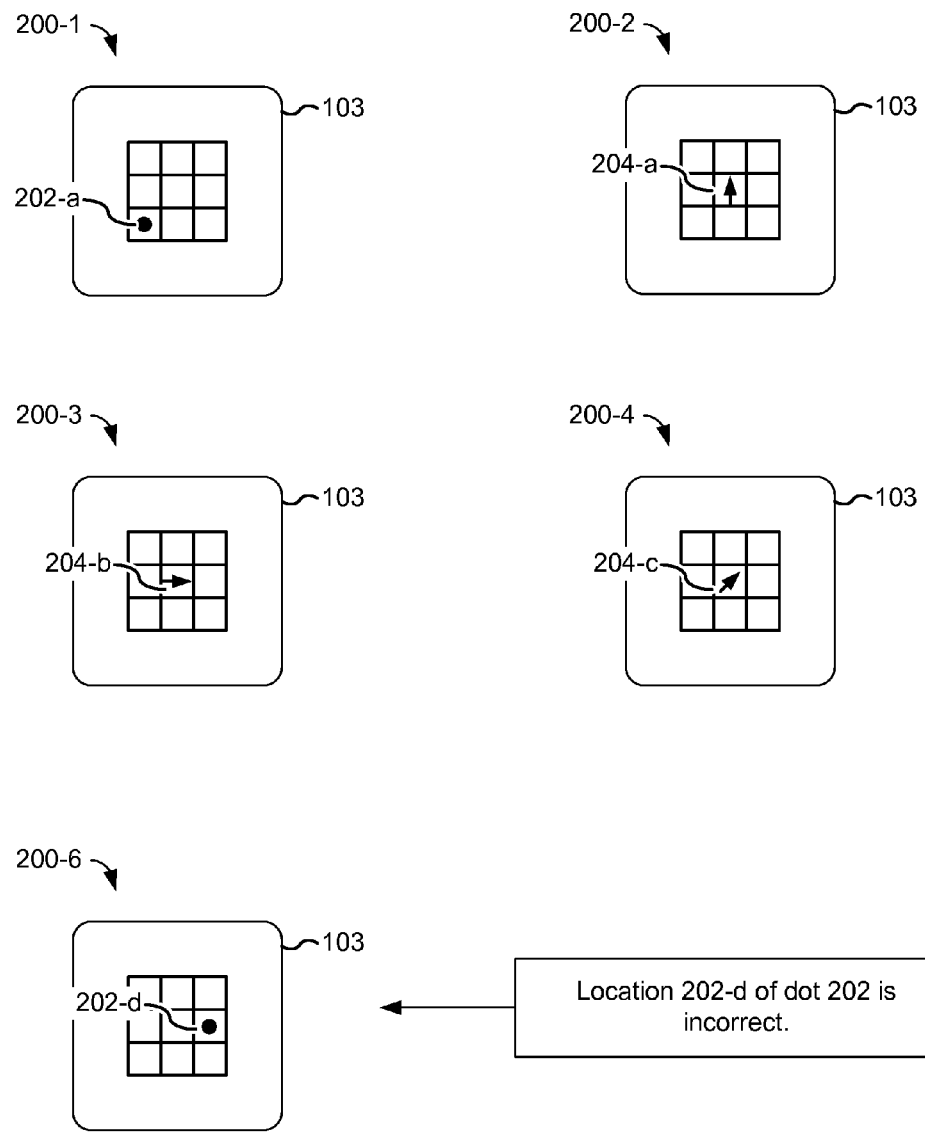

FIGS. 2A-2B illustrate examples of a so-called "spatial working memory" cognitive training game. The goal of this game is to remember the path of a dot on a rectangular grid.

FIGS. 2A-2B each illustrate a trial comprising a plurality of visual stimuli 200. The visual stimuli 200 are displayed sequentially in region 103. For example, in FIG. 2A, stimulus 200-1 is displayed first, stimulus 200-2 is displayed second, stimulus 200-3 is displayed third, stimulus 200-4 is displayed fourth, and stimulus 200-5 is displayed last.

Region 103 is moved periodically within the subject's field of view, as described with reference to FIG. 1, FIGS. 5A-5D and FIGS. 6A-6D.

As shown in FIG. 2A, the subject is shown a dot 202 in an initial location 202-a on a 3×3 grid (alternatively, the grid could be 5×5, 3×5, or more generally n×m, where n and m are positive integers). Dot 202 disappears and the subject is a shown series of arrows 204 (e.g., up-arrow 204-a, right arrow 204-b, and up-right-arrow 204-c) in the center of the grid (alternatively, arrows 204 can be displayed outside the grid, at another location within the grid, or at a random location). Each arrow 204 indicates a movement of dot 202 on the grid. Following this, the subject is again shown dot 202 at a location 202-b on the grid. The subject is prompted to actuate a user input device (e.g., press a key on a keyboard) if the location 202-b matches the destination of dot 202 as indicated by arrows 204. Otherwise, the user is prompted to forgo actuating the user input device. In FIG. 2A, the location 202-b is correct. Thus, the user should actuate the user input device in order to a record a correct response.

FIG. 2B is analogous to FIG. 2A, except that rather than stimulus 200-5 showing the correct location 202-b, FIG. 2B illustrates a stimulus 200-6 showing dot 202 in an incorrect location 202-d. Thus, the user should forgo actuating the user input device in order to a record a correct rejection.

In some embodiments, a game comprises a predefined number of trials (e.g., 10 trials) and the subject is scored based on his or her performance for the game (e.g., a performance index is calculated based on recorded information corresponding to the subject's responses). In some embodiments, a number of correct responses $H_1$ is recorded for the game (e.g., a number of times that the final location of the dot was correct and the subject actuated the user input device), a number of incorrect rejections $M_1$ is recorded (e.g., a number of times the final location of the dot was correct and the subject did not actuate the user input device), a number of incorrect responses $F_1$ is recorded (e.g., a number of times the final location of the dot was not correct and the subject actuated the user input device), and/or a number of correct rejections $C_1$ is recorded (e.g., the final location of the dot was incorrect and the user did not actuate the user input device). In some embodiments, a performance index $P_1$ is calculated using the equation:

$$P_1 = \frac{H_1 + C_1}{H_1 + C_1 + F_1 + M_1}.$$

In some embodiments, the game is repeated while varying a difficulty parameter for the game. In some embodiments, the cognitive training game is repeated using a staircase procedure. Namely, in some embodiments, the cognitive training game is repeated at a higher difficulty level if the performance index $P_1$ of the subject for one or more games exceeds a first threshold. The cognitive training game is repeated at a reduced level of difficulty if the performance index $P_1$ in one or more games is below a second threshold (e.g., the second threshold is distinct from the first threshold, and a performance index below the second threshold indicates a lower level of performance than a performance index above the first threshold). Otherwise, the difficulty of the game is left unchanged. In some embodiments, the cognitive training game is repeated at a higher difficulty level based on one game, but is repeated at a lower difficulty level only if the subject's performance is poor in several consecutive games (e.g., three games). This framework is designed to motivate the subject to continue playing the cognitive training games.

In some embodiments, the difficulty parameters include one or more of a time per arrow (e.g., a time for which each arrow is displayed on the screen, such as 2.0, 1.5, 1.0, 0.75, or 0.5 seconds), a number of arrows per trial (e.g., how many arrows are displayed after dot 202 disappears and before dot 202 reappears, such as 1, 2, 3, 4, 5, 6, or 7 arrows), and a logical value indicating whether the grid is shown when the arrows are displayed (in some circumstances, the absence of the grid makes it harder for a subject to track dot 202).

Figure 3A:
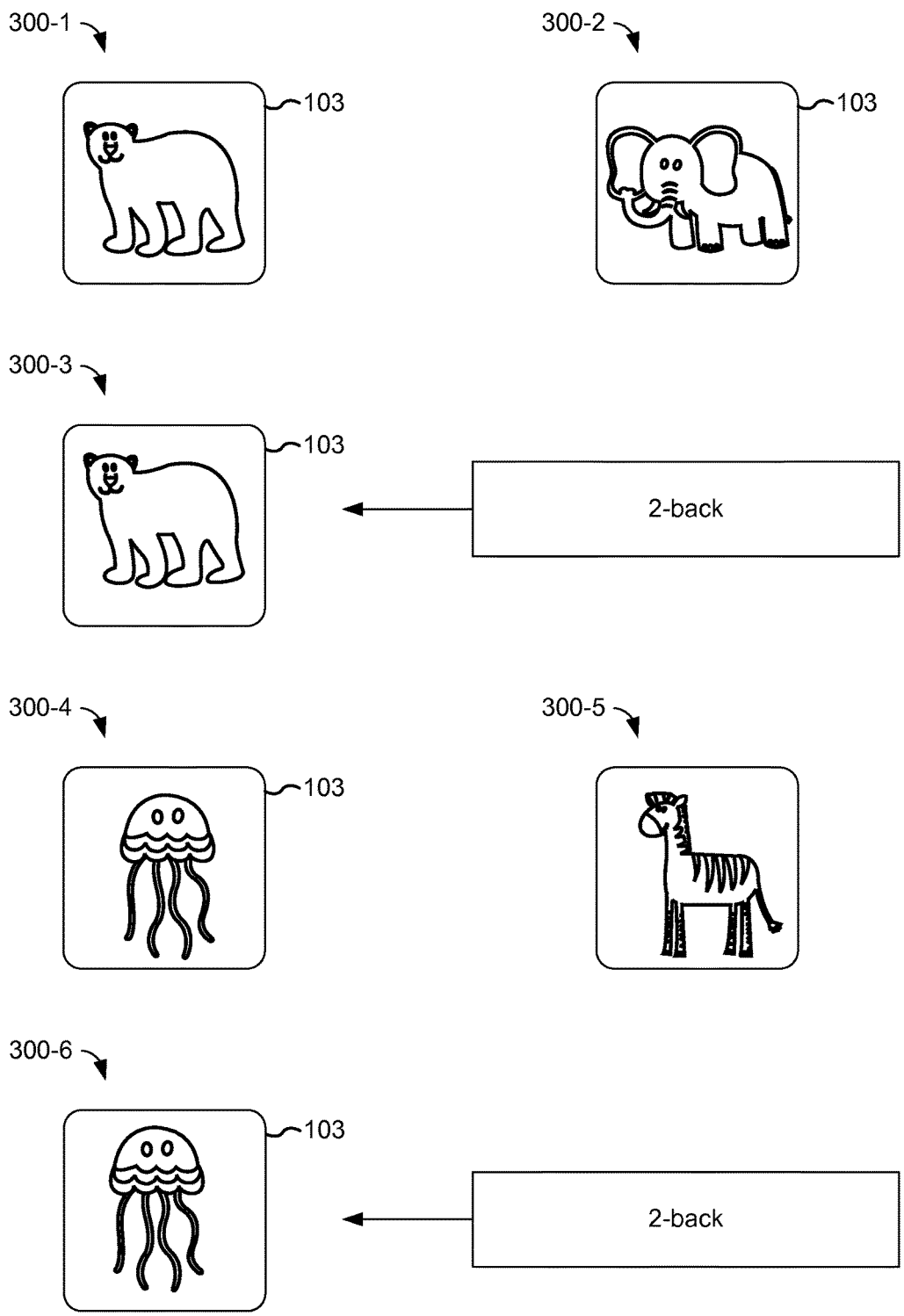
FIGS. 3A-3B illustrate examples of a so-called "n-back" cognitive training game, in accordance with some embodiments.
Figure 3B:
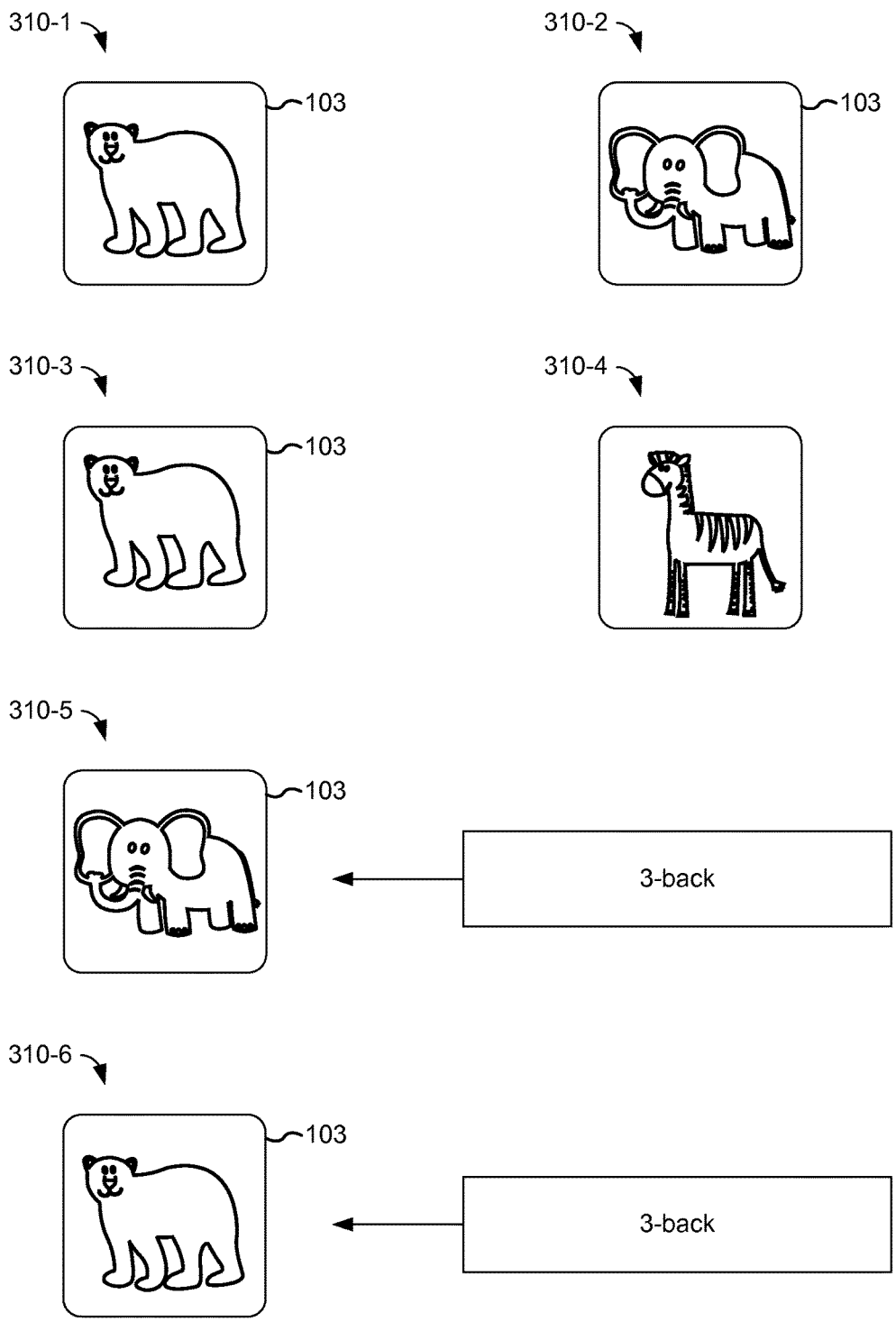

FIGS. 3A-3B illustrate examples of a so-called "n-back" cognitive training game in which the subject is shown a series of stimuli (e.g., images) that are sequentially displayed. The subject is instructed to actuate the user input device when a respective stimulus is the same as an image that was shown n-stimuli ago.

FIG. 3A illustrates a 2-back game in which a plurality of visual stimuli 300 is sequentially displayed. For example, stimulus 300-1 is displayed first, stimulus 300-2 is displayed second, stimulus 300-3 is displayed third, stimulus 300-4 is displayed fourth, stimulus 300-5 is displayed fifth, and stimulus 300-6 is displayed last. The visual stimuli 300 are displayed sequentially in region 103 (see FIG. 1). Region 103 is moved periodically within the subject's field of view, as described with reference to FIG. 1, FIGS. 5A-5D and FIGS. 6A-6D.

In FIG. 3A, the subject's task is to actuate the user input device if a respective stimuli 300 that is currently displayed is the same as the image that was shown 2-stimuli ago. Therefore, the user should actuate the user input device when stimuli 300-3 is shown (because it is the same image as 300-1) and should actuate the user input device when 300-6 is shown (because it is the same image as 300-4). On the other hand, the user should forgo actuating the user input device when stimuli 300-1, 300-2, 300-4, and 300-5 are shown because they are not the same image as an image that was shown 2-stimuli ago.

FIG. 3B illustrates a 3-back game in which a plurality of visual stimuli 310 is sequentially displayed. For example, stimulus 310-1 is displayed first, stimulus 310-2 is displayed second, stimulus 310-3 is displayed third, stimulus 310-4 is displayed fourth, stimulus 310-5 is displayed fifth, and stimulus 310-6 is displayed last. The visual stimuli 310 are displayed sequentially in region 103. Region 103 is moved periodically within the subject's field of view, as described with reference to FIG. 1, FIGS. 5A-5D and FIGS. 6A-6D.

In FIG. 3B, the subject's task is to actuate the user input device if a respective stimulus 310 that is currently displayed is the same as the image that was shown 3-stimuli ago. Therefore, the user should actuate the user input device when stimuli 310-5 is shown (because it is the same image as 310-2) and should actuate the user input device when 310-6 is shown (because it is the same image as 310-3). On the other hand, the user should forgo actuating the user input device when stimuli 310-1, 310-2, 310-3, and 310-4 are shown because they are not the same image as an image that was shown 3-stimuli ago.

In some embodiments, the game proceeds for a predetermined number of stimuli (e.g., 10 stimuli, 100 stimuli) and the subject is scored based on his or her performance for the game (e.g., a performance index is calculated based on recorded information corresponding to the subject's responses). In some embodiments, a number of correct responses $H_2$ is recorded for the game (e.g., a number of times the subject correctly actuated the user input device when a respective stimulus did correspond to a previous stimulus that occurred n-stimuli prior to the respective stimulus), a number of incorrect rejections $M_2$ is recorded (e.g., a number of times that the subject incorrectly forewent actuating (i.e., incorrectly did not actuate) the user input device in response to a respective stimulus, which did correspond to a previous stimulus that occurred n-stimuli prior to the respective stimulus), a number of incorrect responses $F_2$ is recorded (e.g., a number of times the subject incorrectly actuated the user input device despite the fact that a respective stimulus did not actually correspond to a previous stimulus that occurred n-stimuli prior to the respective stimulus), and/or a number of correct rejections $C_2$ is recorded (e.g., a number of times the subject correctly forewent actuating (i.e., correctly did not actuate) the user input device in response to a respective stimulus since the respective stimulus did not correspond to a previous stimulus that occurred n-stimuli prior to the respective stimulus). In some embodiments, a performance index $P_2$ is calculated using the equation:

$$P_2 = \frac{H_2 + C_2}{H_2 + C_2 + M_2 + F_2}.$$

In some embodiments, the game is repeated while varying a difficulty parameter for the game. Namely, in some embodiments, the cognitive training game is repeated at a higher difficulty level if the performance index $P_2$ of the subject for one or more games exceeds a first threshold. The cognitive training game is repeated at a reduced level of difficulty if the performance index $P_2$ in one or more games is below a second threshold (e.g., the second threshold is distinct from the first threshold, and a performance index below the second threshold indicates a lower level of performance than a performance index above the first threshold). Otherwise, the difficulty of the game is left unchanged. In some embodiments, the cognitive training game is repeated at a higher difficulty level based on one game, but is repeated at a lower difficulty level only if the subject's performance is poor in several consecutive games (e.g., three games). This framework is designed to motivate the subject to continue playing the cognitive training games.

In some embodiments, the difficulty parameters include one or more of: a time for which each stimulus is displayed (e.g., 2.0 second, 1.5 second, 1.0 second, 0.75 second) and a level n of the n-back game (also known as a "load factor").

Figure 4A:
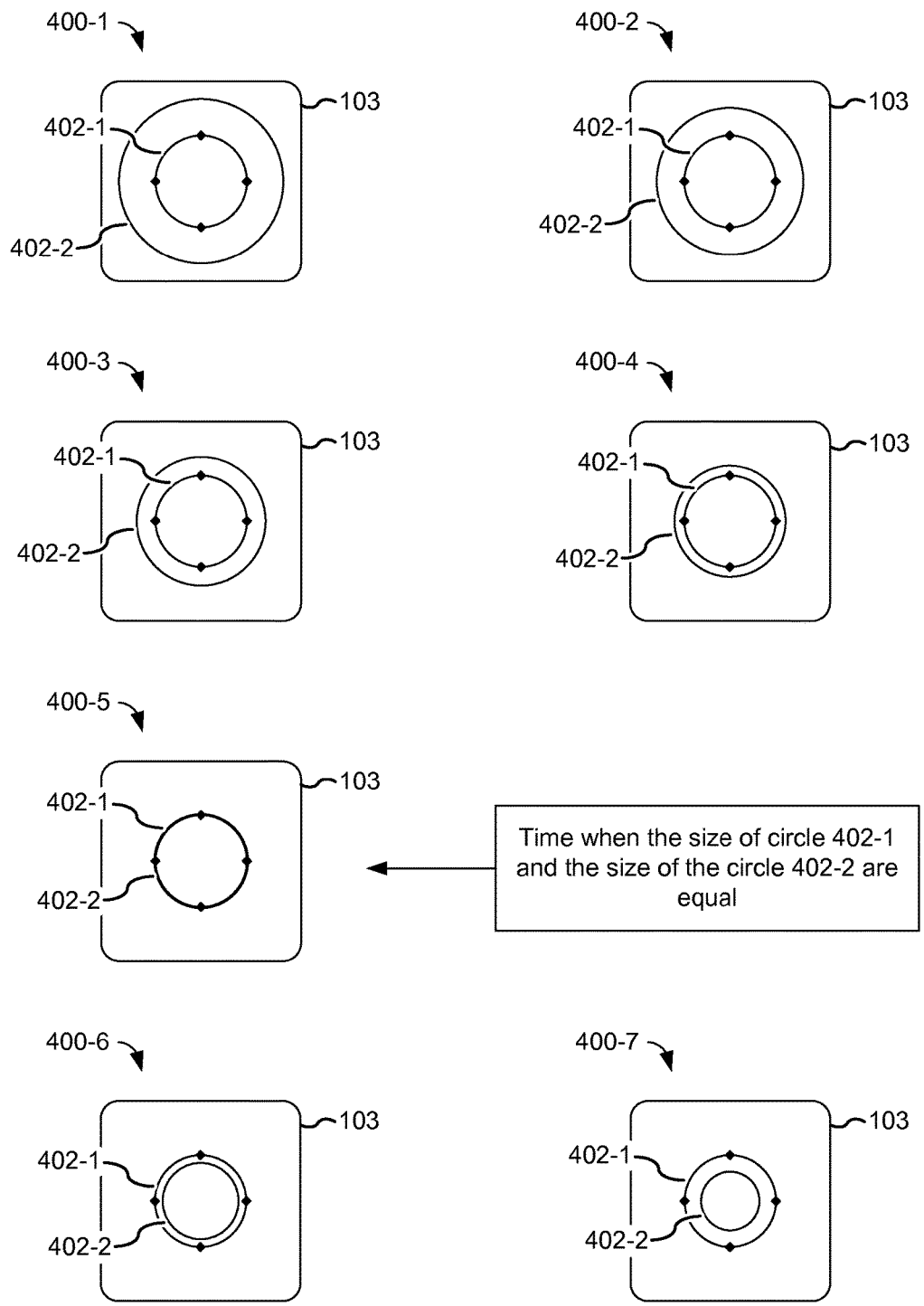
FIGS. 4A-4B illustrate examples of a so-called "intersecting circles" cognitive training game, in accordance with some embodiments.
Figure 4B:
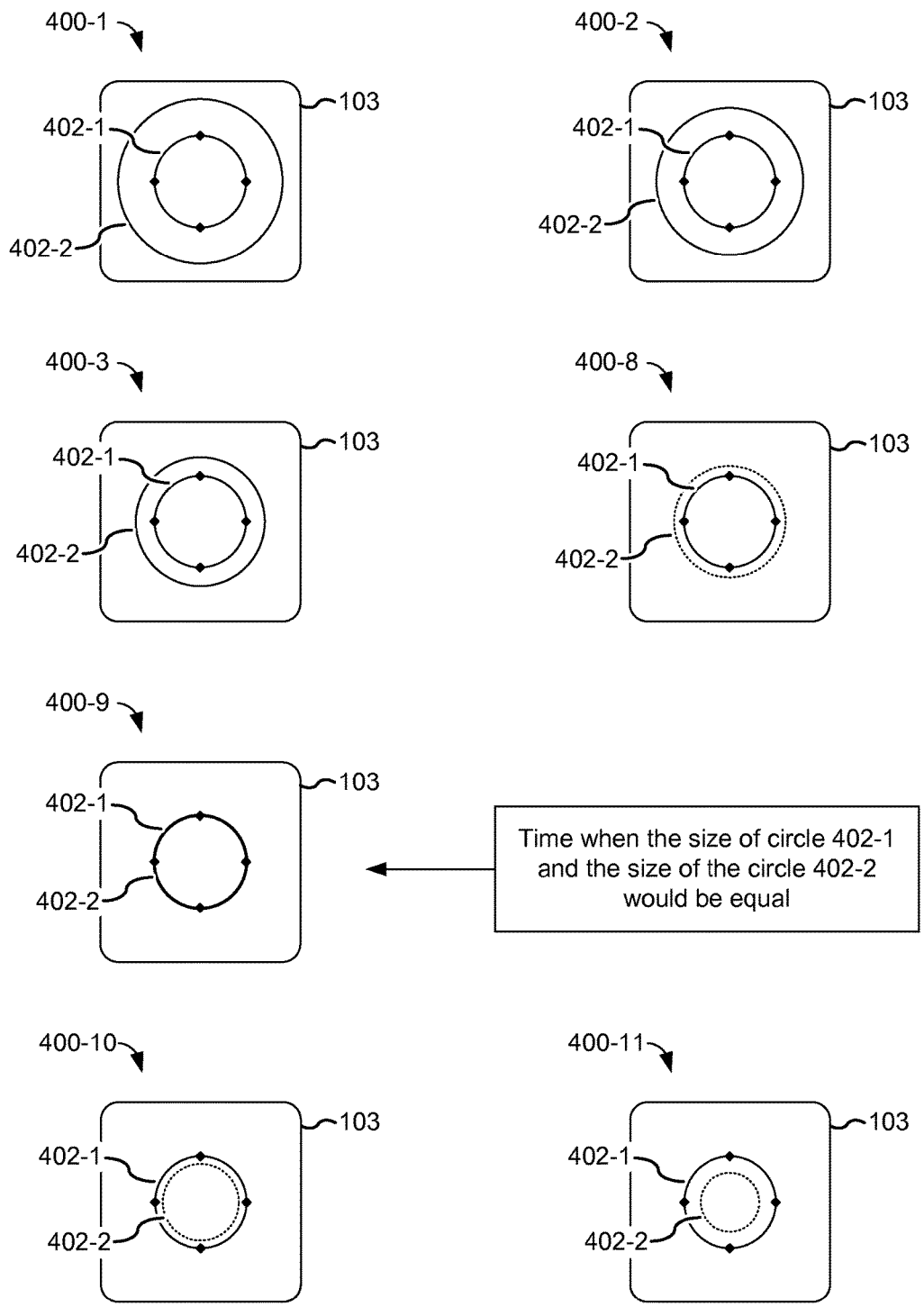

FIGS. 4A-4B illustrate examples of a so-called "intersecting circles" cognitive training game. In the game, two concentric circles are displayed and the difference in their size is reduced over time. The goal of the game is to detect when two circles are the same size (or would be the same size, as explained below). The subject is instructed to actuate the user input device when the two circles are the same size, or would be the same size. Among other things, this game trains the subject to improve his or her predictive timing.

FIGS. 4A-4B each illustrate a trial comprising a plurality of visual stimuli 400. The visual stimuli 400 are displayed sequentially in region 103. For example, in FIG. 4A, stimulus 400-1 is displayed first, stimulus 400-2 is displayed second, stimulus 400-3 is displayed third, stimulus 400-4 is displayed fourth, stimulus 400-5 is displayed fifth, stimulus 400-6 is displayed six, and stimulus 400-7 is displayed last. Region 103 is moved periodically within the subject's field of view, as described with reference to FIG. 1, FIGS. 5A-5D and FIGS. 6A-6D.

In FIG. 4A, each stimuli includes a displayed circle 402-1 and a displayed circle 402-2 that is concentric with circle 402-1. In each subsequent stimulus, a size of the circle 402-2 is changed relative to a size of the circle 402-1 such as to reduce a difference in the size of the circle 402-1 and the size of the circle 402-2. The subject is prompted to actuate the user input device when the size of the circle 402-1 and the size of the circle 402-2 are equal which, in this example, is when stimulus 400-5 is displayed.

FIG. 4B is analogous to FIG. 4A, except that stimuli 400-8, 400-9, 400-10, and 400-11 are displayed in FIG. 4B in lieu of stimuli 400-4, 400-5, 400-6, and 400-7, respectively. In stimuli 400-8, 400-9, 400-10, and 400-11, display of circle 402-2 has been discontinued (to represent the fact that circle 402-2 is no longer displayed, circle 402-2 is depicted with a dashed line). In this example, the subject is tasked with predicting when circle 402-1 and circle 402-2 would be the same size which, in this example, is when stimulus 400-9 is displayed.

It should be understood that the size of the circle 402-2 can be changed relative to the size of the circle 402-1 by changing the size of circle 402-1, changing the size of circle 402-2, or a combination thereof.

In some embodiments, a game comprises a predefined number of trials (e.g., 10 trials) and the subject is scored based on his or her performance for the game (e.g., a performance index is calculated based on recorded information corresponding to the subject's responses).

In some embodiments, a number of correct responses $H_3$ is recorded for the game (e.g., a number of times that the subject actuates the user input device within a predefined threshold, e.g., 0.15 seconds, of the time when two circles are, or would be, the same size) and a number of incorrect responses $M_3$ is recorded (e.g., a number of times that the subject actuates the user input device outside of the predefined threshold of the time when two circles are, or would be, the same size). In some embodiments, a performance index $P_3$ is calculated using the equation:

$$P_3 = \frac{H_3}{H_3 + M_3}.$$

Alternatively, in some embodiments, for each respective trial, a result is calculated and recorded corresponding to a difference in the time when the user actuated the user input device and the time when the two circles are the same size. In some embodiments, a performance index $P_4$ is calculated based on a variability metric associated with a plurality of such results (e.g., all of the results from a single game). In some embodiments, the performance index $P_4$ is calculated based on the standard deviation of the plurality of such results.

In some embodiments, the game is repeated while varying a difficulty parameter for the game. Namely, in some embodiments, the cognitive training game is repeated at a higher difficulty level if the performance index $P_3$ (or alternatively, $P_4$) of the subject for one or more games exceeds a first threshold. The cognitive training game is repeated at a reduced level of difficulty if the performance index $P_3$ (or alternatively, $P_4$) in one or more games is below a second threshold (e.g., the second threshold is distinct from the first threshold, and a performance index below the second threshold indicates a lower level of performance than a performance index above the first threshold). Otherwise, the difficulty of the game is left unchanged. In some embodiments, the cognitive training game is repeated at a higher difficulty level based on one game, but is repeated at a lower difficulty level only if the subject's performance is poor in several consecutive games (e.g., three games). This framework is designed to motivate the subject to continue playing the cognitive training games.

In some embodiments, the difficulty parameters include one or more of: a speed at which the circles converge in size and an amount of time during which only one of the circles is shown.

Figure 5A:
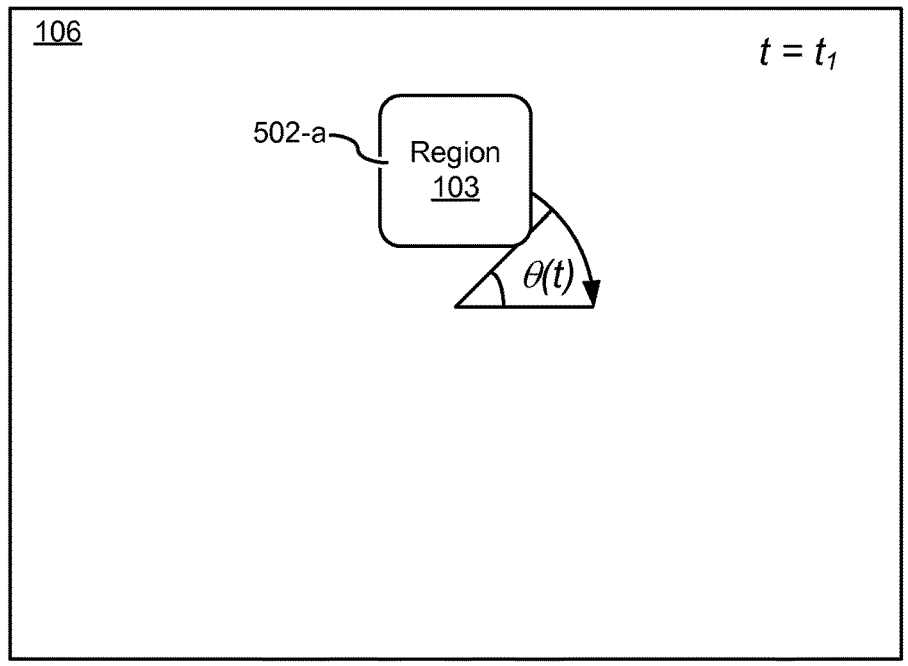
FIGS. 5A-5D illustrate movement of a region along a circular tracking path of a display, in accordance with some embodiments.
Figure 5B:
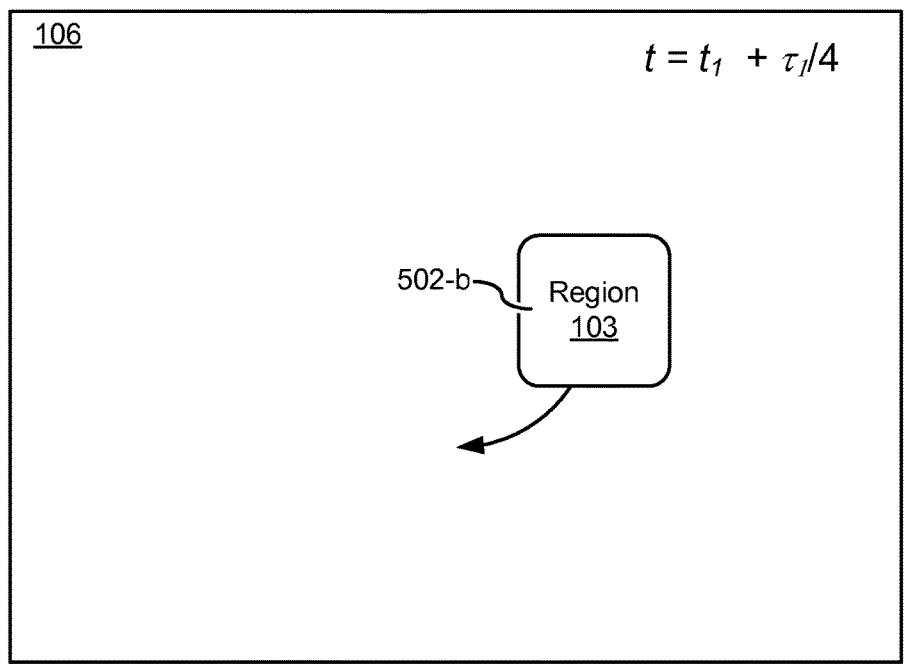
Figure 5C:
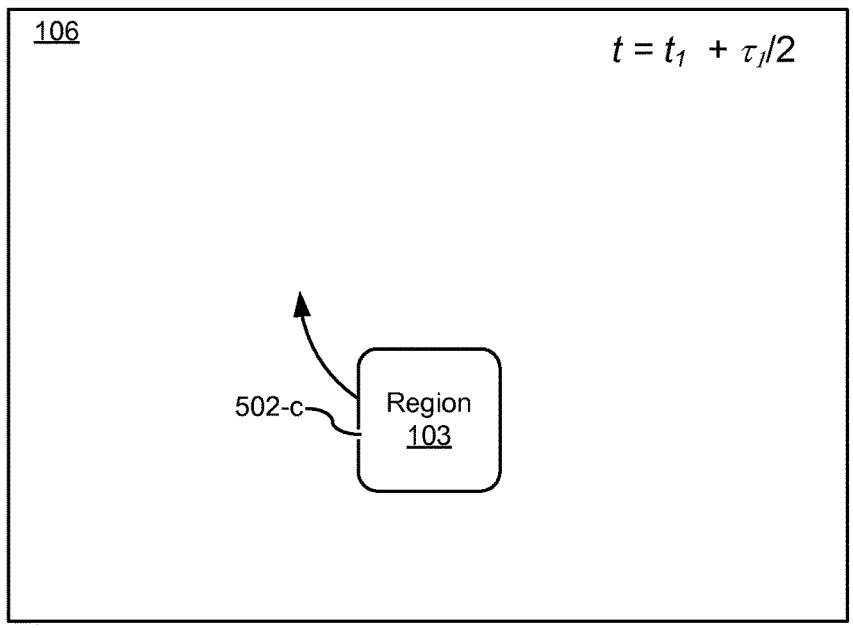
Figure 5D:
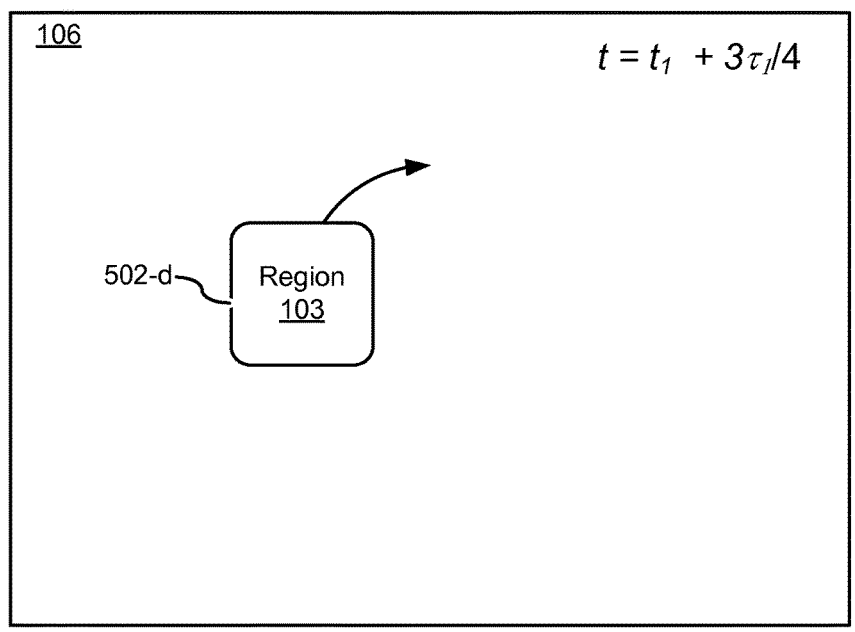

FIGS. 5A-5D illustrate movement of region 103 along a tracking path (e.g., tracking path 114, FIG. 1) of display 106 in accordance with some embodiments. In some embodiments (as shown in FIGS. 5A-5D), the tracking path is circular, meaning that the movement of region 103 is along a circle having a fixed radius and can be described by an angular variable $\theta(t)$ where t is time. In some embodiments, the movement of region 103 is periodic with a period $\tau_1$. In some embodiments, periodic means that $\theta(t)=\theta(t+\tau_1)$ for any t in the range, $t_i < t < t_f - \tau_1$ ($t_1$ being an initial time of periodic movement and $t_f$ being a final time of periodic movement). To that end, FIG. 5A shows region 103 at a location 502-a along the tracking path at a time $t_1$, where $t_i < t_1 < t_f - \tau_1$. FIG. 5B shows region 103 at a location 502-b along the tracking path at a time $t_1 + \tau_1/4$. FIG. 5C shows region 103 at a location 502-c along the tracking path at a time $t_1 + \tau_1/2$. Finally, FIG. 5D shows region 103 at a location 502-d along the tracking path at a time $t_1 + 3\tau_1/4$. In some embodiments, $\theta(t)=2\pi f \times (t-t_1)$, where f is a frequency (e.g., f=0.4 Hz).

Figure 6A:
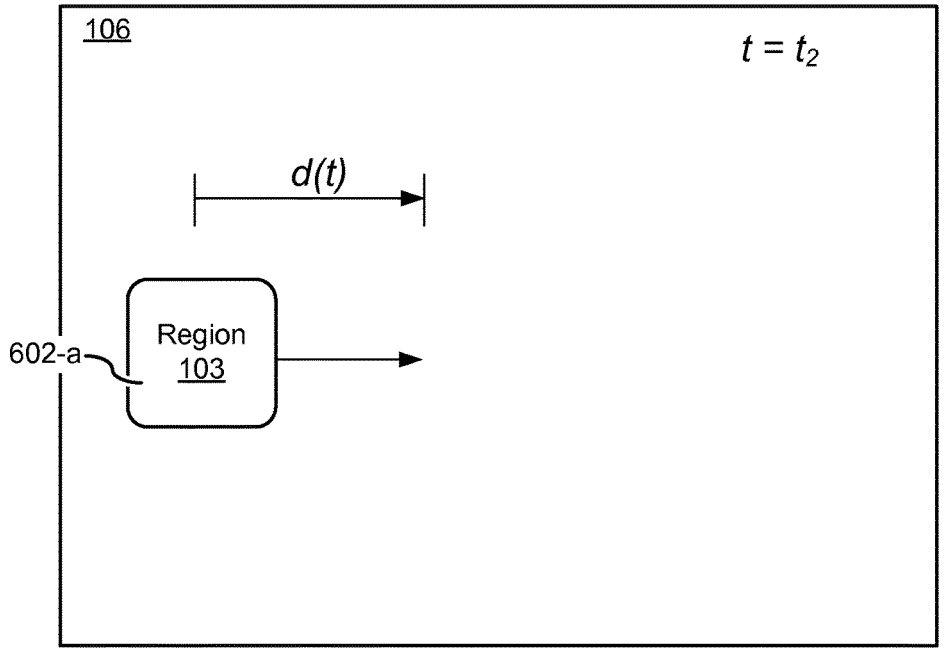
FIGS. 6A-6D illustrate movement of a region along a linear tracking path of a display, in accordance with some embodiments.
Figure 6B:
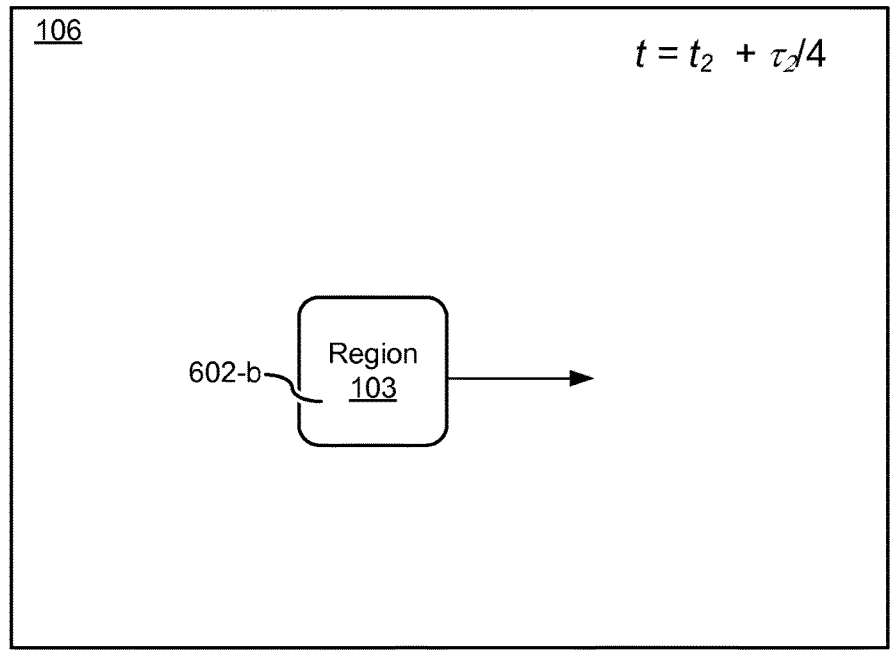
Figure 6C:
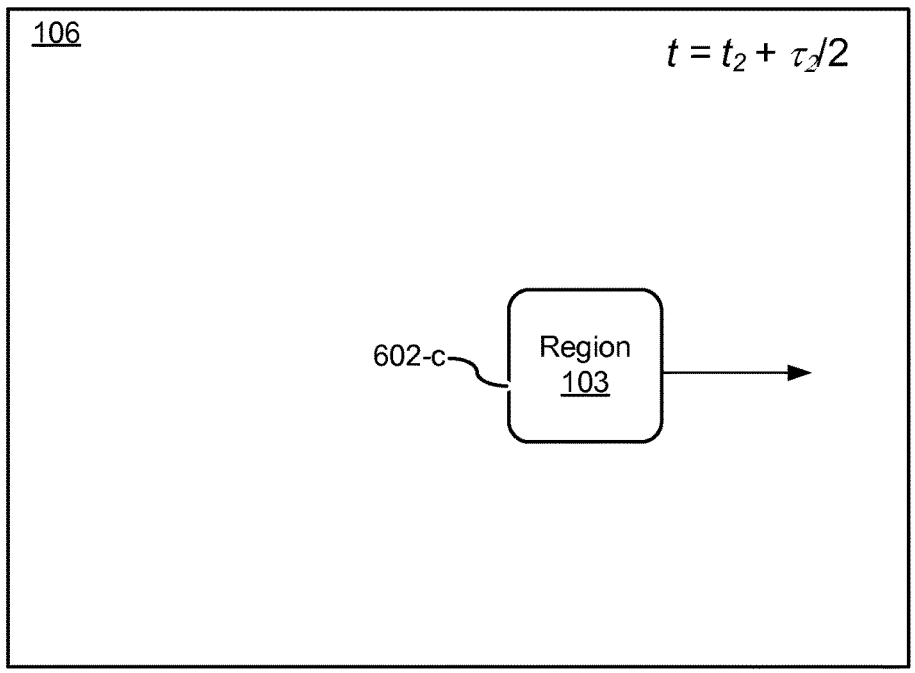
Figure 6D:
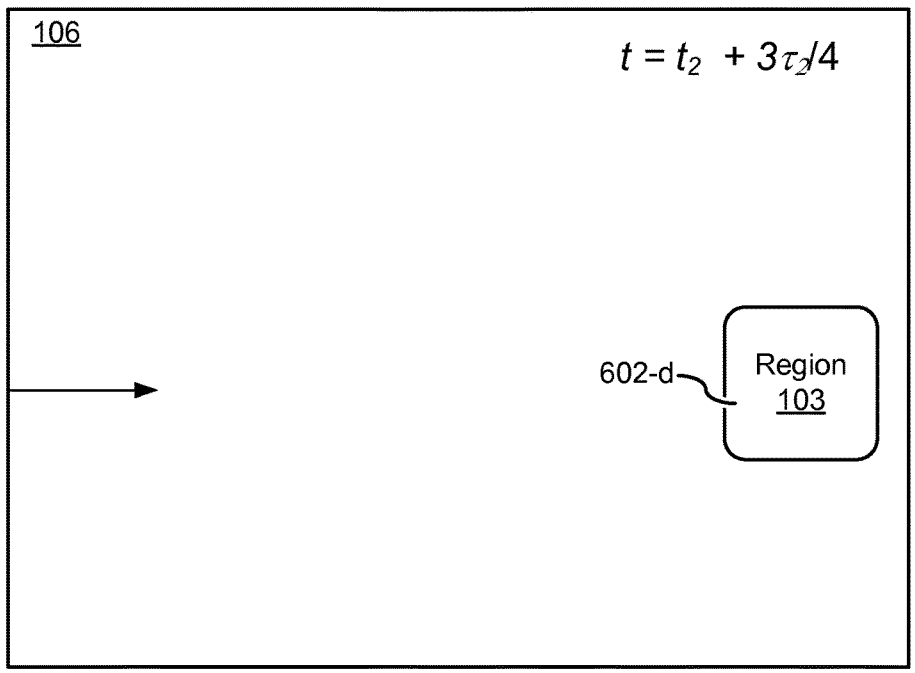

FIGS. 6A-6D illustrate movement of region 103 along a tracking path (e.g., tracking path 114, FIG. 1) of display 106 in accordance with some embodiments. In some embodiments (as shown in FIGS. 6A-6D), the tracking path is linear, meaning that the movement of region 103 is along a line and can be described by a distance variable d(t) where t is time. In some embodiments, the movement of region 103 is periodic with a period $\tau_2$. In some embodiments, periodic means that $d(t)=d(t+\tau_2)$ for any t in the range, $t_i < t < t_f - \tau_2$ ($t_i$ being an initial time of periodic movement and $t_f$ being a final time of periodic movement). To that end, FIG. 6A shows region 103 at a location 602-a along the tracking path at a time $t_2$, where $t_i < t_2 < t_f - \tau_2$. FIG. 6B shows region 103 at a location 602-b along the tracking path at a time $t_2 + \tau_2/4$. FIG. 6C shows region 103 at a location 602-c along the tracking path at a time $t_2 + \tau_2/2$. Finally, FIG. 6D shows region 103 at a location 602-d along the tracking path at a time $t_2 + 3\tau_2/4$.

It should be understood that the tracking paths depicted in FIGS. 5A-5D and FIGS. 6A-6D are merely exemplary. One of ordinary skills in the art will understand that any arbitrary tracking path x(t) may be used, where x(t) represents coordinates of region 103 on display 106 at a time t. Furthermore, in some embodiments, the movement of the region 103 along the arbitrary tracking path x(t) is periodic with an arbitrary period r. In some embodiments, periodic means that $x(t)=x(t+\tau)$ for any t in the range, $t_i < t < t_f - \tau$ ($t_i$ being an initial time of periodic movement and $t_f$ being a final time of periodic movement). In some embodiments, the movement of the region 103 along the arbitrary tracking path x(t) is quasi-periodic such that it is visually predictable to a subject.

Moreover, periodic movement should be construed to mean movement that appears regular, predictable, or periodic to a normal (e.g., healthy) subject.

In some embodiments, a plurality of visual stimuli are sequentially displayed in a region 103 as it is moved periodically along the arbitrary tracking path x(t). In some embodiments, a subject is prompted to respond to a task associated with the sequential display of the plurality of visual stimuli. For example, the subject may be asked to play any of the games illustrated in FIGS. 2A-2B, FIGS. 3A-3B, or FIGS. 4A-4B (e.g., the plurality of stimuli may include stimuli analogous to those shown in FIGS. 2A-2B, FIGS. 3A-3B, or FIGS. 4A-4B and that subject may be asked to respond in a manner consistent with the description of the corresponding game, as described above).

Figure 7A:
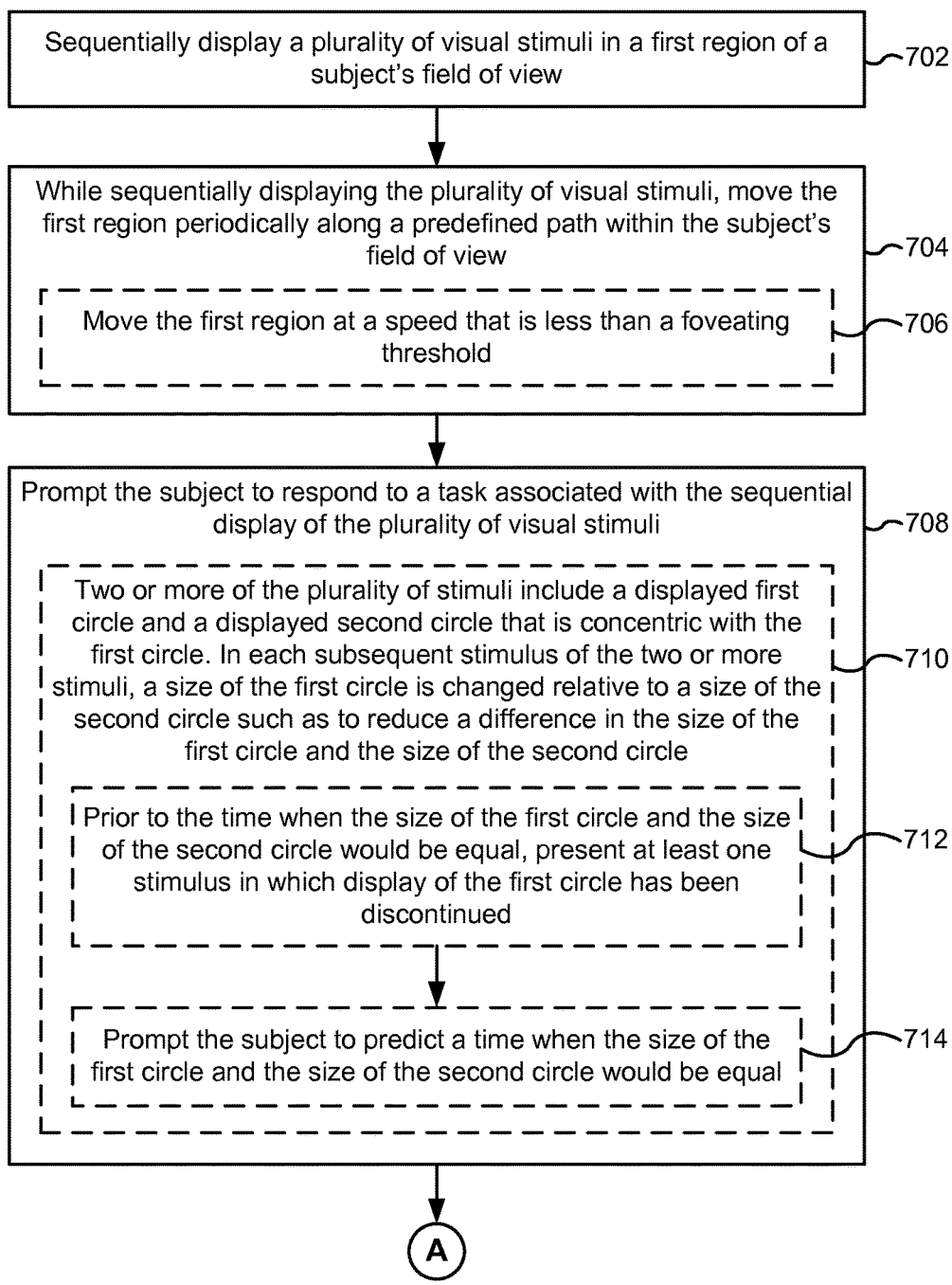
FIGS. 7A-7C illustrate a flow diagram of a method for dynamic cognitive training, in accordance with some embodiments.
Figure 7B:
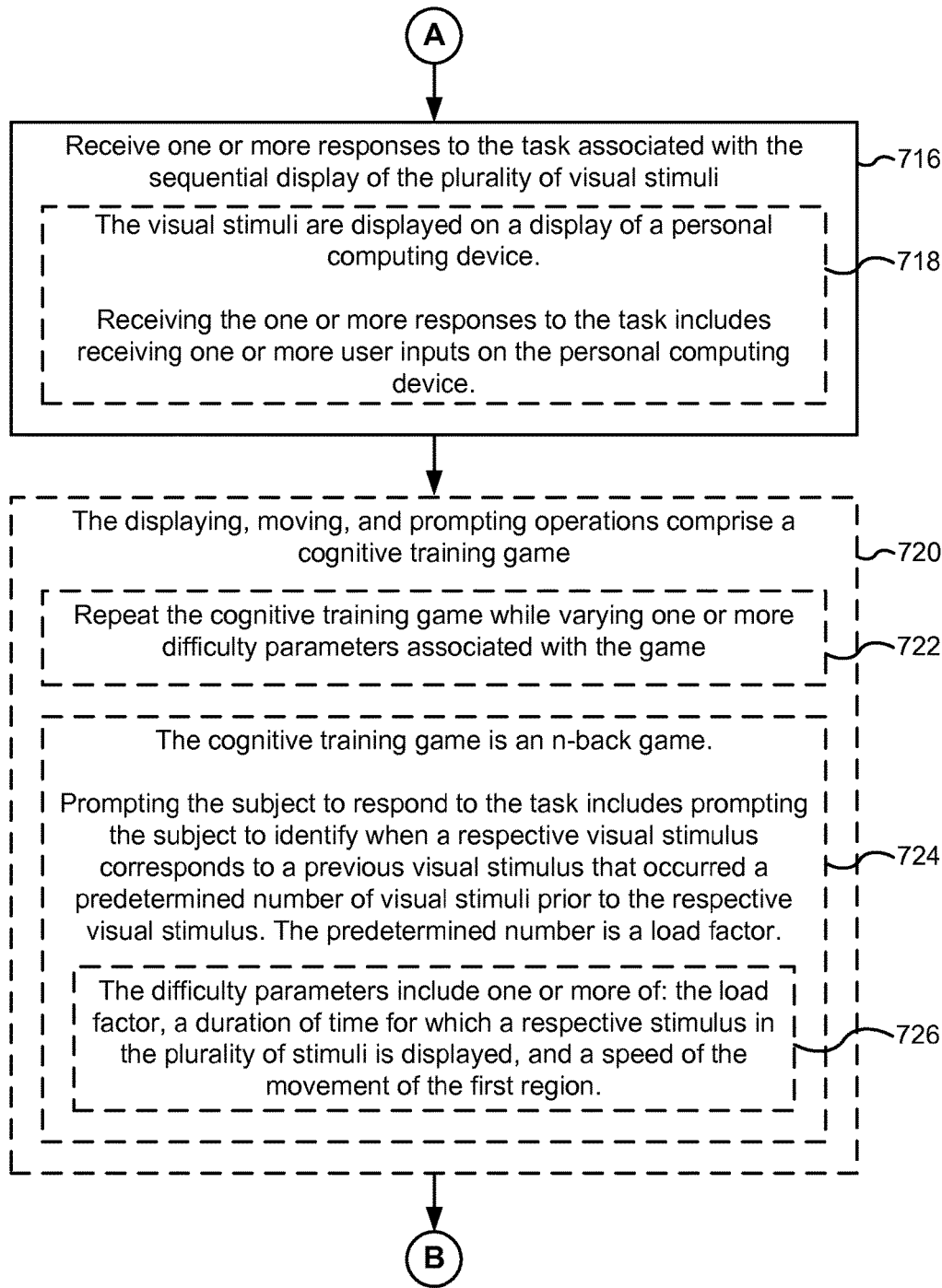
Figure 7C:
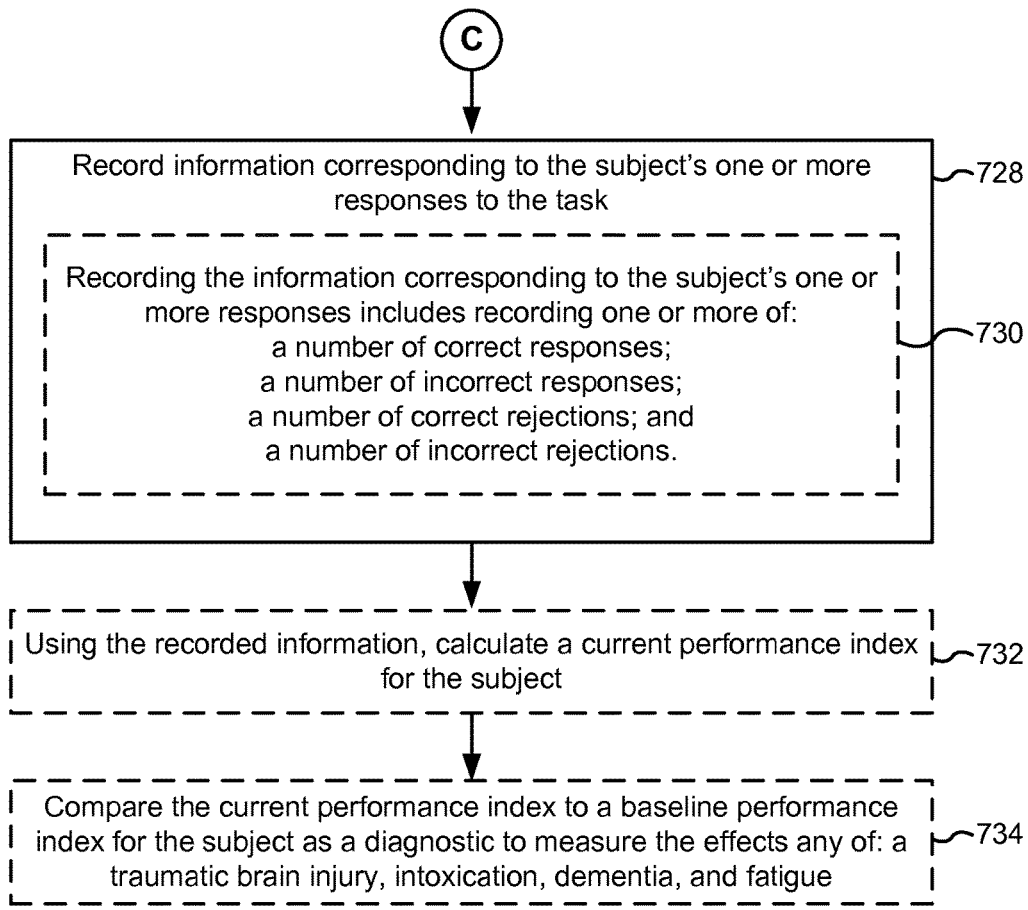
Figure 8:
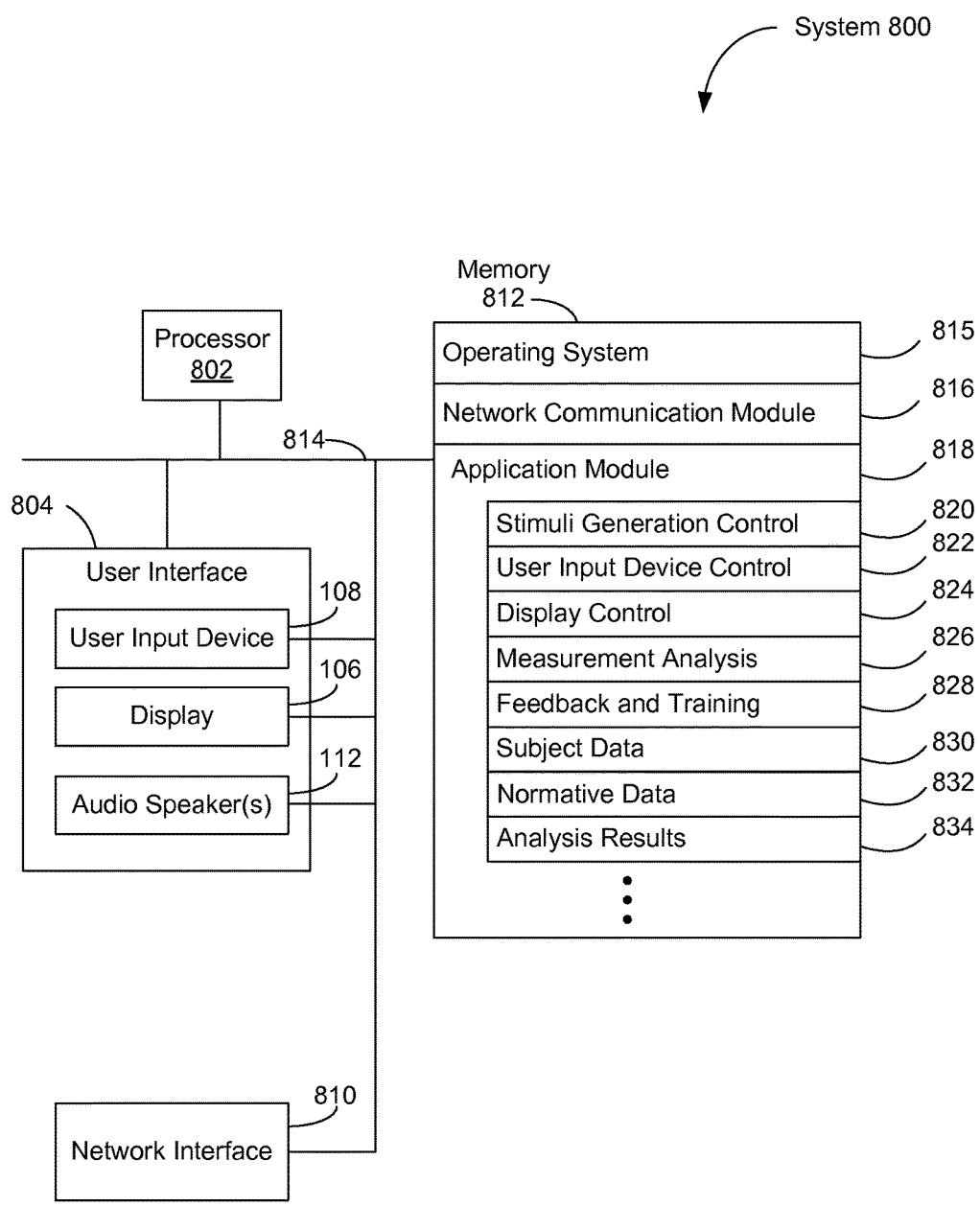
FIG. 8 is a block diagram of a system for dynamic cognitive training, in accordance with some embodiments.

FIGS. 7A-7C illustrate a flow diagram of a method 700 for dynamic cognitive training, in accordance with some embodiments. Method 700 is, optionally, governed by instructions that are stored in a computer memory or non-transitory computer readable storage medium (e.g., memory 812 in FIG. 8) and that are executed by one or more processors (e.g., processor(s) 802) of one or more computer systems, including, but not limited to, system 100 (FIG. 1) and/or system 800 (FIG. 8). The computer readable storage medium may include a magnetic or optical disk storage device, solid state storage devices such as Flash memory, or other non-volatile memory device or devices. The computer readable instructions stored on the computer readable storage medium may include one or more of: source code, assembly language code, object code, or other instruction format that is interpreted by one or more processors. In various implementations, some operations of method 700 may be combined and/or the order of some operations may be changed from the order shown in the figures. Also, in some implementations, operations shown in separate figures and/or discussed in association with separate methods may be combined to form other methods, and operations shown in the same figure and/or discussed in association with the same method may be separated into different methods. Moreover, in some implementations, one or more operations in the methods are performed by modules of system 800 shown in FIG. 8, including, for example, processor(s) 802, user interface 804, memory 812, network interface 810, and/or any sub modules thereof.

In some implementations, method 700 is performed at a system including one or more processors and memory storing instructions for execution by the one or more processors (e.g., system 100 or system 800). Method 700 includes sequentially displaying (702) a plurality of visual stimuli in a first region of a subject's field of view.

While sequentially displaying the plurality of visual stimuli, the system moves (704) the first region periodically along a predefined path within the subject's field of view. For example, the first region traverses the predefined path more than once (e.g., the first region traverses the predefined path 1.1 times, 2 times, 8 times, etc.). In some embodiments, the movement of the first region along the predefined path is described by the function x(t), which is periodic with a period τ. In some embodiments, periodic means that $x(t)=x(t+\tau)$ for any t in the range, $t_i < t < t_f - \tau$ ($t_i$ being an initial time of periodic movement and $t_f$ being a final time of periodic movement). In some embodiments, the movement of the first region along the predefined path is quasi-periodic such that it is visually predictable to a subject.

In some embodiments, the first region is moved (706) at a speed that is less than a foveating threshold (e.g., the first region is moved at a speed that is slow enough to allow the subject to track the first region using smooth eye pursuit). For example, in some implementations, the predefined path is a circular path with a radius such that the circular path encompasses a visual angle of 5 degrees as viewed by the subject. It is found that, in such circumstances, when the first region moves along the predefined path at a rate between 10 and 160 degrees per second, a "normal" subject is able to track the first region using smooth eye pursuit.

The system prompts (708) the subject to respond to a task associated with the sequential display of the plurality of visual stimuli. In some embodiments, two or more of the plurality of stimuli include (710) a displayed first circle and a displayed second circle that is concentric with the first circle. In each subsequent stimulus of the two or more stimuli, a size of the first circle is changed relative to a size of the second circle such as to reduce a difference in the size of the first circle and the size of the second circle. In some embodiments, prior to the time when the size of the first circle and the size of the second circle would be equal, the system presents (712) at least one stimulus in which display of the first circle has been discontinued. In some embodiments, the system prompts (714) the subject to predict a time when the size of the first circle and the size of the second circle would be equal.

The system receives (716) one or more responses to the task associated with the sequential display of the plurality of visual stimuli. In some embodiments, the visual stimuli are displayed (718) on a display of a personal computing device and receiving the one or more responses to the task includes receiving one or more user inputs on the personal computing device.

In some embodiments, the displaying, moving, and prompting operations comprise (720) a cognitive training game. In some embodiments, the system repeats (722) the cognitive training game while varying one or more difficulty parameters associated with the game. In some embodiments, the cognitive training game is repeated using a staircase procedure. Namely, in some embodiments, the cognitive training game is repeated at a higher difficulty level if a performance index of the subject for one or more games exceeds a first threshold. The cognitive training game is repeated at a reduced level of difficulty if the performance index in one or more games is below a second threshold (e.g., the second threshold is distinct from the first threshold, and a performance index below the second threshold indicates a lower level of performance than a performance index above the first threshold). Otherwise, the difficulty of the game is left unchanged. In some embodiments, the cognitive training game is repeated at a higher difficulty level based on one game, but is repeated at a lower difficulty level only if the subject's performance is poor in several consecutive games (e.g., three games). This framework is designed to motivate the subject to continue playing the cognitive training games.

In some embodiments, the cognitive training game is (724) an n-back game and prompting the subject to respond to the task includes prompting the subject to identify when a respective visual stimulus corresponds to a previous visual stimulus that occurred a predetermined number of visual stimuli prior to the respective visual stimulus. The predetermined number is a load factor. The difficulty parameters include (726) one or more of: the load factor, a duration of time for which a respective stimulus in the plurality of stimuli is displayed, and a speed of the movement of the first region.

In some embodiments, the n-back game is a two-back game, in which the subject is asked to identify when a respective visual stimulus corresponds to a visual stimulus that occurred two stimuli back. For example, the sequence of visual stimuli for the two-back game may comprise the following sequences of images: a dog, a cat, a mouse, a lion, a fox, and a lion. The subject would then appropriately respond to the task by indicating that the second occurrence of the lion meets the "two-back" criteria, in that it is the same image as the imaged that was displayed two stimuli ago. In some embodiments, the n-back game is a two-back game in which the subject is presented with a sequence of paired numbers. The subject is then prompted to identify when the sum of a respective pair of numbers is equal to a sum of a previous pair of numbers that occurred two stimuli back from the respective pair.

The system records (728) information corresponding to the subject's one or more responses to the task associated with the sequential display of the plurality of visual stimuli. For example, for an n-back game, the system records (730) one or more of: a number of correct responses, a number of incorrect responses, a number of correct rejections, and a number of incorrect rejections. In some implementations, a correct response signifies that the subject correctly identified a respective visual stimulus, meaning that the respective stimulus did indeed correspond to a previous visual stimulus that occurred n-stimuli prior to the respective visual stimulus. In some implementations, an incorrect response signifies that the subject incorrectly identified a respective visual stimulus, meaning that the subject responded despite the fact that respective stimulus did not actually correspond to a previous visual stimulus that occurred n-stimuli prior to the respective visual stimulus. In some implementations, a correct rejection signifies that the subject correctly forewent responding (i.e., correctly did not respond) to a respective visual stimulus since the respective visual stimulus did not correspond to a previous visual stimulus that occurred n-stimuli prior to the respective visual stimulus. In some implementations, an incorrect rejection signifies that the subject incorrectly forewent responding (i.e., incorrectly did not respond) to a respective visual stimulus, which did in fact correspond to a previous visual stimulus that occurred n-stimuli prior to the respective visual stimulus.

In some embodiments, using the recorded information, the system calculates (732) a current performance index for the subject. In some embodiments, the system compares (734) the current performance index to a baseline performance index for the subject as a diagnostic to measure the effects any of: a traumatic brain injury, intoxication, dementia, and fatigue. For example, in some embodiments, if the current performance index is less than the baseline performance index by at least (or, alternatively, more than) a predefined threshold, the system makes an assessment that the user's performance has declined (e.g., if compared against a baseline performance index of the subject) or is impaired (e.g., if compared against a baseline performance index of a control group).

In some embodiments, the baseline performance index is based on at least one of: performance associated with a preselected group of control subjects (sometimes called a control group baseline), a demographic of the subject (e.g., an age range, a gender, a socio-economic status, etc.), and a performance index for the subject generated from a previous test (sometimes called an individual or personal baseline). For example, an individual or personal baseline may be obtained for a football player at the beginning of a season, or a military person prior to deployment. In the event that such a person suffers a potential traumatic brain injury, a current performance index can be generated for the person as described above and compared with their respective individual baseline. In this manner, a convenient, low-cost indication of a person's cognitive ability is provided, and the severity of their traumatic brain injury can be assessed.

In some circumstances, a control group baseline can be used to calibrate a field sobriety test that utilizes the methods and games described above. For example, the system may comprise a tablet computer storing instructions that cause the tablet computer to perform method 700. A current performance index for a suspect of a "driving under the influence" (DUI) offense can be calculated and compared with a baseline performance index associated with a preselected group of control subjects as a manner in which to perform the field sobriety test. This type of field sobriety test is advantageous over conventional field sobriety tests (e.g., having the suspect stand on one foot and count backwards) because the tablet computer can record data (e.g., the suspect's responses, the suspect's performance index, a date and time, etc.) that may be of greater evidentiary value than a law enforcement officials qualitative testimony alone.

FIG. 8 is a block diagram of a system 800 for dynamic cognitive training, in accordance with some embodiments. In some embodiments, system 800 shares one or more components with system 100 described with reference to FIG. 1 (e.g., display 106, user input device, and audio speaker(s) 112). While certain specific features are illustrated, those skilled in the art will appreciate from the present disclosure that various other features have not been illustrated for the sake of brevity and so as not to obscure more pertinent aspects of the implementations disclosed herein.

To that end, the system includes one or more processor(s) 802 (e.g., CPUs), user interface 804, memory 812, and one or more communication buses 814 for interconnecting these components. In some embodiments, the system includes one or more network or other communications interfaces 810. The user interface 804 includes display 106, user input device 108, and audio speaker(s) 112. In some implementations, display 106 is a touch-screen display, obviating the need for a user input device 108.

The communication buses 814 may include circuitry (sometimes called a chipset) that interconnects and controls communications between system components. Memory 812 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 812 may optionally include one or more storage devices remotely located from the processor(s) 802. Memory 812, including the non-volatile and volatile memory device(s) within memory 812, comprises a non-transitory computer readable storage medium.

In some implementations, memory 812 or the non-transitory computer readable storage medium of memory 812 stores the following programs, modules and data structures, or a subset thereof, including an operating system 815, a network communication module 816, and an application module 818.

The operating system 815 includes procedures for handling various basic system services and for performing hardware dependent tasks.

The network communication module 816 facilitates communication with other devices via the one or more communication network interfaces 810 (wired or wireless) and one or more communication networks, such as the Internet, other wide area networks, local area networks, metropolitan area networks, and so on.

In some embodiments, application module 818 includes stimuli generation module 820, user input device control module 822, display control module 824, measurement analysis module 826, and, feedback and training module 828. Stimuli generation module generates stimuli that are displayed in region 103 of display 106 (see FIG. 1). In some embodiments, stimuli generation module generates the stimuli in accordance with a random process and/or in accordance with one or more difficulty parameters. Display control module 822 controls display 106 in order to provide displayed stimuli. Measurement analysis module 826 analyzes the subject's responses to the stimuli to produce measurements and analyses, as discussed elsewhere in this document.

In some embodiments, application module 818 also stores subject data 830, which includes measurement data for a subject, analysis results 834 and the like. Subject measurement data can be used to generate a personal baseline against which a performance index of the subject is compared. In some embodiments, application module 818 stores normative data 832, which includes measurement data from one or more control groups of subjects, and optionally includes analysis results 834, and the like, based on the measurement data from the one or more control groups. In some embodiments, this control group measurement data can be used to generate a baseline value against which a performance index of the subject is compared (e.g., to measure the effects any of a traumatic brain injury, intoxication, dementia, and/or fatigue). In some embodiments, the control groups include one or more control group subjects that match a demographic of the subject (e.g., an age range, gender, socioeconomic status, etc.) In some embodiments, application module 818 is a mobile application on a portable multifunction device (e.g., a smart-phone) that serves to inform its user's (e.g., based on their responses to the stimuli) about their cognitive ability to, for example, operate a vehicle. In some embodiments, application module 818 is a mobile application on a portable multifunction device that serves to inform athletic medical personnel about an athlete's readiness to return to play after suffering a potential mild traumatic brain injury.

In some embodiments, feedback and training module 828 utilizes any of the methods and games described above (e.g., method 700, FIG. 7 and/or any of the games described with reference to FIGS. 2A-2B, 3A-3B, and 4A-4B, or a combination thereof) as cognitive training games to improve attention and white matter connectivity in brain regions that are associated with attention and working memory. To this end, in some circumstances, a subject will be instructed to undergo a dynamic brain training regiment by completing, for example, one 30 minute session per day for each day over a period of six to eight weeks (e.g., by running feedback and training module 828 on a personal computing device). In particular, feedback and training module 828 interacts with stimuli generation control module 820 to modify the difficulty of the generated stimuli in accordance with the subject's performance. In some embodiments, feedback and training module 828 will vary one or more difficulty parameters associated with the games over the course of a respective 30 minute session and/or throughout the period of six to eight weeks (e.g., using subject data 830). In some embodiments, feedback and training module 828 will utilize a staircase procedure as described above with reference to operation 722 as a manner through which to vary the one or more difficulty parameters. The staircase procedure provides a framework that motivates the subject to continue playing and improves their ability to succeed in increasingly difficult cognitive training games. As noted above, since anticipatory cognition and movement timing are controlled by essentially the same brain circuits, an increased ability to succeed in these cognitive training yields transferable effects such as a greater attention and working memory.

In some embodiments, not shown, the system shown in FIG. 8 is divided into two systems, one which measures a subject and collects data, and another which receives the collected data and analyzes the data (e.g., a server system).

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

It will be understood that, although the terms "first," "second," etc. may be used herein to describe various elements, these elements should not be limited by these terms. These terms are only used to distinguish one element from another. For example, a first widget could be termed a second widget, and, similarly, a second widget could be termed a first widget, without changing the meaning of the description, so long as all occurrences of the "first widget" are renamed consistently and all occurrences of the "second widget" are renamed consistently. The first widget and the second widget are both widgets, but they are not the same widget.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "upon a determination that" or "in response to determining" or "in accordance with a determination" or "upon detecting" or "in response to detecting" that the stated condition precedent is true, depending on the context.

What is claimed is:

1. A method of visual cognitive training, performed by a computer system having a display, memory, and one or more user input devices, the method comprising:
   displaying on the display, in a first region of a subject's field of view, a cognitive training game comprising sequential display of a plurality of visual stimuli and a task having one or more correct responses relating to the sequential display of the plurality of visual stimuli;
   while sequentially displaying the plurality of visual stimuli, moving the first region in which the cognitive training game is displayed periodically along a predefined path on the display;
   receiving, via the one or more user input devices, one or more responses to the task relating to the sequential display of the plurality of visual stimuli in the cognitive training game;
   recording in the memory information corresponding to the subject's one or more responses to the task;
   using the recorded information, calculating a current performance index for the subject; and
   comparing the current performance index to a baseline performance index for the subject or for a control group as a diagnostic to measure the effects of any of: a traumatic brain injury, intoxication, dementia, and fatigue.

2. The method of claim 1, wherein moving the first region in which the cognitive training game is displayed periodically along the predefined path on the display further comprises moving the first region at a speed that is less than a foveating threshold.

3. The method of claim 1, wherein:
   the computer system is a personal computing device.

4. The method of claim 1, wherein:
   the cognitive training game is an n-back game; and
   the task includes identifying when a respective visual stimulus corresponds to a previous visual stimulus that occurred a predetermined number of visual stimuli prior to the respective visual stimulus, the predetermined number comprising a load factor.

5. The method of claim 4, wherein recording the information corresponding to the subject's one or more responses includes recording one or more of:
   a number of correct responses;
   a number of incorrect responses;
   a number of correct rejections; and
   a number of incorrect rejections.

6. The method of claim 1, further including repeating the cognitive training game while varying one or more difficulty parameters associated with the game.

7. The method of claim 6, wherein the difficulty parameters include one or more of: a load factor, a duration of time for which a respective stimulus in the plurality of stimuli is displayed, and a speed of the movement of the first region.

8. The method of claim 1, wherein:
   two or more of the plurality of stimuli include a displayed first circle and a displayed second circle that is concentric with the first circle;
   in each subsequent stimulus of the two or more stimuli, a size of the first circle is changed relative to a size of the second circle such as to reduce a difference in the size of the first circle and the size of the second circle; and
   the task includes predicting a time when the size of the first circle and the size of the second circle would be equal.

9. The method of claim 8, further including, prior to the time when the size of the first circle and the size of the second circle would be equal, presenting at least one stimulus in which display of the first circle has been discontinued.

10. A system for visual cognitive training, comprising:
    one or more processors;
    a display;
    one or more user input devices;
    memory; and one or more programs stored in the memory, the one or more programs comprising instructions that when executed by the one or more processors cause the system to:
- display on the display, in a first region of a subject's field of view, a cognitive training game comprising sequential display of a plurality of visual stimuli and a task having one or more correct responses relating to the sequential display of the plurality of visual stimuli;
- while sequentially displaying the plurality of visual stimuli, move the first region in which the cognitive training game is displayed periodically along a predefined path on the display;
- receive, via the one or more user input devices, one or more responses to the task relating to the sequential display of the plurality of visual stimuli in the cognitive training game;
- record in the memory information corresponding to the subject's one or more responses to the task;
- using the recorded information, calculate a current performance index for the subject; and
- compare the current performance index to a baseline performance index for the subject or for a control group as a diagnostic to measure the effects of any of: a traumatic brain injury, intoxication, dementia, and fatigue.

11. The system of claim 10, wherein the instructions cause the first region in which the cognitive training game is displayed to move at a speed that is less than a foveating threshold.

12. The system of claim 10, wherein:
the system includes a personal computing device.

13. The system of claim 10, wherein:
the cognitive training game is an n-back game; and
the task includes identifying when a respective visual stimulus corresponds to a previous visual stimulus that occurred a predetermined number of visual stimuli prior to the respective visual stimulus, the predetermined number comprising a load factor.

14. The system of claim 13, wherein the instructions for recording the information corresponding to the subject's one or more responses include instructions for recording one or more of:
a number of correct responses;
a number of incorrect responses;
a number of correct rejections; and
a number of incorrect rejections.

15. The system of claim 10, further including instructions that cause the system to repeat the cognitive training game while varying one or more difficulty parameters associated with the game.

16. The system of claim 15, wherein the difficulty parameters include one or more of: a load factor, a duration of time for which a respective stimulus in the plurality of stimuli is displayed, and a speed of the movement of the first region.

17. The system of claim 10, wherein:
two or more of the plurality of stimuli include a displayed first circle and a displayed second circle that is concentric with the first circle;
in each subsequent stimulus of the two or more stimuli, a size of the first circle is changed relative to a size of the second circle such as to reduce a difference in the size of the first circle and the size of the second circle; and
the task includes predicting a time when the size of the first circle and the size of the second circle would be equal.

18. The system of claim 17, further including instructions that, prior to the time when the size of the first circle and the size of the second circle would be equal, cause the system to present at least one stimulus in which display of the first circle has been discontinued.

19. A non-transitory computer readable storage medium storing one or more programs, the one or more programs comprising instructions, which when executed by an electronic system with a display, memory, and one or more user input devices, cause the system to:
- display on the display, in a first region of a subject's field of view, a cognitive training game comprising sequential display of a plurality of visual stimuli and a task having one or more correct responses relating to the sequential display of the plurality of visual stimuli;
- while sequentially displaying the plurality of visual stimuli, move the first region in which the cognitive training game is displayed periodically along a predefined path on the display;
- receive, via the one or more user input devices, one or more responses to the task relating to the sequential display of the plurality of visual stimuli in the cognitive training game;
- record in the memory information corresponding to the subject's one or more responses to the task;
- using the recorded information, calculate a current performance index for the subject; and
- compare the current performance index to a baseline performance index for the subject or for a control group as a diagnostic to measure the effects of any of: a traumatic brain injury, intoxication, dementia, and fatigue.

20. The non-transitory computer readable storage medium of claim 19, wherein the instructions cause the first region to move on the display at a speed that is less than a foveating threshold.

* * * * *